United States Patent [19]

Scholze et al.

[11] 4,243,692

[45] Jan. 6, 1981

[54] PROCESS FOR THE PRODUCTION OF SILICIC ACID HETEROPOLYCONDENSATES USEFUL AS COATING MATERIALS

[75] Inventors: Horst Scholze, Würzburg; Helmut Schmidt, Höchberg, both of Fed. Rep. of Germany

[73] Assignee: Fraunhofer-Gesellschaft, Munich, Fed. Rep. of Germany

[21] Appl. No.: 973,559

[22] Filed: Dec. 27, 1978

[30] Foreign Application Priority Data

Dec. 28, 1977 [DE] Fed. Rep. of Germany ....... 2758414

[51] Int. Cl.³ ............................................. C08G 77/56
[52] U.S. Cl. ......................................... 427/2; 528/13; 528/17; 528/18; 528/31; 528/32; 435/7; 435/176; 435/240; 424/12; 23/230 B; 428/447
[58] Field of Search ................. 528/13, 17, 18, 31, 528/32; 435/240; 424/12; 428/447; 427/2

[56] References Cited

U.S. PATENT DOCUMENTS

| | | | |
|---|---|---|---|
| 2,446,135 | 7/1948 | Hyde | 528/39 |
| 2,470,562 | 5/1949 | Hyde | 528/39 |
| 2,486,162 | 10/1949 | Hyde | 528/39 |
| 2,857,356 | 10/1958 | Goodwin, Jr. | 528/39 |
| 2,873,265 | 2/1959 | Rust | 528/39 |
| 3,310,417 | 3/1967 | Lerner et al. | 528/39 |
| 3,403,050 | 9/1968 | Chadha | 528/39 |
| 3,489,782 | 1/1970 | Pruvost et al. | 528/10 |

*Primary Examiner*—Sam Silverberg
*Attorney, Agent, or Firm*—Oblon, Fisher, Spivak, McClelland & Maier

[57] ABSTRACT

A process for the production of silicic acid heteropolycondensates wherein at least one substituted silane; at least one functional silane; at least one hydrolysable silicic acid derivative and optionally at least one substantially involatile oxide soluble in the reaction medium, or a compound convertible thereto, are condensed in the presence of at least the quantity of water stoichiometrically required for hydrolysis and optionally in the presence of a condensation catalyst and/or a solvent.

The heteropolycondensates prepared by this process are useful in the preparation of coatings for substrates, which coated substrates are useful as supports in the culture of living cells.

23 Claims, No Drawings

PROCESS FOR THE PRODUCTION OF SILICIC ACID HETEROPOLYCONDENSATES USEFUL AS COATING MATERIALS

BACKGROUND OF THE INVENTION

This invention relates to new silicic acid heteropolycondensates, to a process for their production and to their use as coating compositions, particularly in the culture of living cells.

Tissue and cell cultures are used for histological cytological, molecular-biological and similar studies, generally being prepared beforehand in suitable nutrient media. Living cells of higher organisms, for example liver cells, are also increasingly being used for pharmacological studies. In this way, it is possible to obtain more relevant test results, i.e. test results which provide a clearer reflection of the actual physiological conditions in the living organisms, than by conventional biochemical test methods. For example, enzyme activity is frequently related to the physiological conditions of a functioning living cell and the active co-operation of the cell wall is necessary for numerous biochemical and biological processes. These in vitro methods using living cell cultures are suitable for example for testing medicaments and for developing specific indicators for cell and ecological poisons.

The culture of living cells often requires special conditions. For example, cells emanating from body tissue have to be grown on mechanical supports which enable the cells to grow within the structure or in close proximity thereto. The use of conventional supports, for example glasses or plastics, involves the problem that the cells show poor adhesion to the support and become detached during culture in nutrient solutions so that the requirement of growth within the structure is not satisfied. This phenomenon is particularly pronounced in cases where highly dilute serums are used as the nutrient solutions.

It has now been found that certain silicic acid heteropolycondensates are particularly suitable for use as coatings on standard support materials, for example glass vessels, for solving the problem stated above, i.e. they provide excellent supports for the preparation of tissue and cell cultures. The cells are firmly bound to the support, presumably through chemical binding forces, so that growth within the cell structure is guaranteed. In addition, the silicic acid heteropolycondensates according to the invention are suitable for various other technical applications.

SUMMARY OF THE INVENTION

The present invention relates to silicic acid heteropolycondensates which can be produced by condensing
(a) at least one substituted silane corresponding to the general formula:

$$SiR_nR''_{(4-n)} \qquad (I)$$

in which R represents hydrogen, halogen, alkoxy or $-NR'_2$ ($R'$=hydrogen and/or lower alkyl), $R''$ represents alkyl, alkenyl, aryl or aralkyl and n is an integer of from 1 to 3;
(b) at least one functional silane corresponding to the general formula:

in which R is as defined above, $R'''$ represents alkylene, phenylene, alkyl phenylene or alkylene phenylene, Y represents halogen or an optionally substituted amino, optionally substituted anilino, aldehyde, keto, carboxy, hydroxy, mercapto, cyano, hydroxyphenyl, diazo, carboxylic acid alkyl ester, sulphonic acid ($-SO_3H$) or phosphoric acid ($-PO_3H_2$) group and n is an integer of from 1 to 3,
(c) at least one hydrolysable silic acid derivative corresponding to the general formula:

in which R is as defined above, with the proviso that not all of the radicals R are hydrogen, and
(d) optionally at least one substantially involatile oxide soluble in the reaction medium or at least one compound of an element of Groups Ia to Va, IVb or Vb of the Periodic System which forms a substantially involatile oxide in the presence of at least the quantity of water stoichiometrically necessary for hydrolysis and, optionally, in the presence of a condensation catalyst and/or a solvent, the quantities in which components (a) to (d) are used being selected in such a way that the silicic acid heteropolycondensate formed contains, based on oxides, from 60 to 90% by weight of component (a); from 1 to 15% by weight of component (b); from 1 to 30% by weight of component (c) and from 0 to 40% by weight of component (d).

Preferred silicic acid heteropolycondensates according to the invention contain, based on oxides,
from 65 to 85% by weight, more particularly from 75 to 80% by weight, of component (a);
from 2 to 10% by weight, more particularly from 4 to 8% by weight, of component (b);
from 5 to 20% by weight, more particularly from 9 to 12% by weight, of component (c) and
from 0 to 20% by weight, more particularly from 0 to 10% by weight, of component (d).

If a component (d) is used, it is employed in a minimum quantity of normally 1, preferably 5 and, more particularly, 9% by weight.

The quantities indicated above relate to the composition of the silicic acid heteropolycondensate in terms of oxide units. In other words, components (a) to (d) are used in such quantities that the particular oxide unit formed by hydrolysis and condensation or the oxide equivalent formed by hydrolysis makes up the indicated proportion by weight (% by weight) in the final condensate. The quantity of hydrolysable silanes corresponding to the formula $R_nSi(OR)_{4-n}$ is calculated for example on the basis of oxide units corresponding to the formula $R_nSiO_{(4-n)/2}$, whereas the oxide equivalent $M_2O$ is the basis for example for metal alcoholates (d) corresponding to the formula MOR.

Apart from the conditions under which condensation is carried out, the quantitative ratio between the starting components (a) to (d) determines the properties of the silicic acid heteropolycondensates obtained and, in particular, the properties of the coatings produced from them. It has been found that the substituted silanes of formula (I) are primarily responsible for the adhesion properties of the coatings on the supports; the functional silanes of formula (II) are responsible for the number of reactive coupling sites on the surface of the coating; the hydrolysable silicic acid derivatives of formula (III) are responsible for the surface quality of the coating, particularly its specific surface, and the oxide component (d) is responsible for the mechanical properties of the coatings. In this connection, it is crucially important to use the hydrolysable silicic acid derivatives of formula (III) in a proportion of less than 30% by weight in order to prevent the silicic acid heteropolycondensates and the coatings produced from them from becoming undesirably porous.

Components (a) and (c) are replaceable insofar as, instead of using a mixture of a dialkyl silane (a) and an orthosilicic acid ester (c), it is possible for example to use an equivalent quantity of a corresponding monoalkyl silane, for example $(CH_3)Si(OC_2H_5)_3$ or $(CH_3)SiCl_3$.

In the definition of the starting compounds of formulae I to III, the several radicals R, R', R'', R''' and Y may be the same or different in each case. The alkyl radicals represent for example straight or branched-chain radicals containing from 1 to 20, preferably 1 to 10 carbon atoms, in particular lower alkyl radicals. Specific examples are methyl, ethyl, n-propyl, isopropyl, n-butyl, sec.-butyl, tert.-butyl, pentyl and n-hexyl.

The aryl radicals contain for example from 6 to 25, preferably from 6 to 14 and, more particularly from 6 to 10 carbon atoms. Specific examples are phenyl and naphthyl, phenyl being preferred. The alkenyl radicals are, for example, straight or branched-chain radicals containing from 2 to 20 carbon atoms, preferably from 2 to 10 carbon atoms, and in particular are lower alkenyl radicals. Specific examples are vinyl or allyl.

The alkylene, alkoxy, alkylamino and aralkyl radicals are derived for example from the above mentioned alkyl and aryl radicals. Specific examples are ethylene, trimethylene, methoxy, ethoxy, and n- and i-propoxy, n-sec.- and tert.-butoxy, monoethylamino, dimethylamino, diethylamino, benzyl and tolyl.

The expression "lower" applies to radicals containing from 1 to 6 carbon atoms, preferably from 1 to 4 carbon atoms and, more particularly from 1 to 2 carbon atoms.

The above-mentioned radicals may contain standard substitutents, for example halogen atoms, lower alkyl, hydroxy, nitro or amino groups.

Of the halogens, fluorine, chlorine and bromine are preferred, chlorine being particularly preferred.

In component (b), n preferably has the value 2 or 3 and, more particularly, the value 3.

Examples of suitable starting silanes corresponding to formula I are $(CH_3)_2SiCl_2$; $(CH_3)_2Si(OCH_3)_2$; $(CH_3)_2Si(OC_2H_5)_2$ and $(C_6H_5)_2SiCl_2$.

Examples of suitable starting silanes corresponding to formula II are $(C_2H_5O)_3Si(CH_2)_3NH_2$ and $(C_2H_5O)_3Si(CH_2)_3CN$.

Examples of suitable starting silanes corresponding to formula III are $(CH_3O)_4Si$; $(C_2H_5O)_4Si$; $SiCl_4$ and $HSiCl_3$.

These silanes may be produced by known methods; cf. W. Noll "Chemie and Technologie der Silicone", Verlag Chemie GmbH, Weinheim/Bergstrasse (1968).

Substantially involatile oxides soluble in the reaction medium or compounds of elements of Groups Ia to Va, IVb or Vb of the Periodic System which form substantially involatile oxides are used as starting component (d). These compounds react with the other components (a) to (c) and, in so doing, make it possible for the chemical and mechanical properties of the silicic acid heteropolycondensates obtained and, in particular, of the coatings produced from them to be modified.

Component (d) is preferably derived from the following elements: Na, K, Mg, Ca, B, Al, Pb, P, As, Ti, Zr and/or V, the elements Na, Ca, Mg, B, Al and P being particularly preferred.

Of the substantially involatile oxides, $Na_2O$, $K_2O$, $CaO$, $B_2O_3$, $As_2O_3$ and $P_2O_5$ are preferred.

Compounds which form substantially involatile oxides soluble in the reaction medium are, for example inorganic acids, such as phosphoric acid and boric acid, and their esters, halides and salts. It is also possible to use hydroxides, such NaOH, KOH or $Ca(OH)_2$ or alkoxides such as NaOR, KOR, $Ca(OR)_2, Al(OR)_3$ $Ti(OR)_4$, R being derived from lower alcohols, such as methanol, ethanol, propanol, or butanol. Other suitable starting compounds are the corresponding salts with volatile acids, for example acetates, basic acetates, formates, nitrates and halides, such as basic lead acetate.

To produce the silicic acid heteropolycondensates, the starting components are mixed in the required quantitative ratio in the absence of moisture optionally in the presence of an organic solvent. Examples of suitable solvents are alcohols, preferably lower alcohols, such as methanol and ethanol, ketones, preferably lower dialkyl ketones, such as acetone and methylisobutyl ketone, ethers, preferably lower dialkyl ethers, such as diethyl ether, amides, such as dimethyl formamide, and mixtures thereof.

The quantity of water stoichiometrically required for hydrolysing the hydrolysable groups present is added either at the same time as the other starting component or afterwards. In the context of the invention, hydrolysable groups are understood to be groups which are hydrolysable under the reaction conditions applied, i.e. Si-O-alkyl, Si-H, Si-halogen, metal-O-alkyl and similar groups. Based on alkoxy substituents, the stoichiometric quantity of water amounts for example to two thirds of the quantity of water required for hydrolysing all of the alkoxy radicals according to formula because one molecule of water is split off for every two alkoxy radicals.

The polycondensation reaction is optionally carried out in the presence of a catalyst, for example a compound which releases protons or hydroxyl ions or an amine. Examples of suitable catalysts are water, acids, preferably volatile acids, such as hydrochloric acid or acetic acid, inorganic bases, such as sodium hydroxide, potassium hydroxide or calcium hydroxide, or lower alkyl amines, such as triethylamine, water and acids being preferred. The catalyst is preferably used in a quantity of up to 3% by weight, based on the reaction mixture.

The polycondensation reaction is normally carried out at a temperature in the range from $-20°$ to $+130°$ C., preferably at a temperature in the range of from 0° to 65° C. and, more particularly, at room temperature. The condensation time is determined by the particular starting components used and the quantities in which they are used, the catalyst used and the reaction temperature. Where acid catalysts are used, shorter condensation times are used.

The process according to the invention is generally carried out in a single stage until condensation is complete. In a preferred embodiment, however, condensation is carried out in two stages by precondensing the starting components for 1 minute to 24 hours under the above-mentioned temperature conditions, optionally in the presence of a catalyst and/or a solvent, and then completing condensation in the presence of at least the quantity of water stoichiometrically required for hydrolysis.

Precondensation is accompanied on the one hand by transalkoxylation of the silanes and, on the other hand, by oligomerisation controllable through the reaction conditions selected, with simultaneous elimination of ether. In this connection, the occurrence of a cyclisation reaction can reduce the number of cross-linkable terminal groups, which inevitably results in a relatively low degree of polymerisation. In general, the precondensation step is continued to such an extent that the precondensate formed is still thinly liquid in consistency, i.e. up to a degree of polymerisation corresponding to about 10 monomer units.

The polycondensation reaction may be carried out under normal pressure, elevated pressure or reduced pressure. The precondensation step may be carried out at reflux temperature in the absence of air.

It is possible, particularly where the silicic acid heteropolycondensates according to the invention are used as coatings, to carry out the post-condensation step by applying the dissolved precondensate to the support either as such or after addition of the quantity of water stoichiometrically required for hydrolysis, evaporating off the solvent present, if any, and optionally treating the layer thus applied with water or steam and/or stoving at elevated temperature.

In this embodiment of the process according to the invention, normally from 5 to 40% by weight, preferably from 10 to 35% by weight and, more particularly, from 25 to 30% by weight solutions of the precondensate are applied to the support either as such or after the addition of the stoichiometric quantity of water. The solvent is evaporated off for example over a period of from 15 to 45 minutes and preferably over a period of from 20 to 40 minutes at elevated temperatures, for example at a temperature of from 75° to 150° C. and preferably at a temperature of from 100° to 120° C. During evaporation, covalent bonds are formed between the silanol groups of the silicic acid heteropolycondensate and reactive groups on the surface of the supports, so that the fully condensed (cross-linked) silicone layer adheres excellently to the support. In order completely to crosslink the silicic acid heteropolycondensate, the layer applied to the support may optionally be after-treated with water or steam. The water or steam may have a temperature of from 4° to 150° C., the stability of the layer increasing with the temperature. The treatment time amounts for example to between 2 and 30 minutes. After-treatment with boiling water for between 10 and 20 minutes has proved to be particularly advantageous. The layer may then optionally be stored for between 5 and 30 minutes and preferably for between 15 and 25 minutes at temperatures of, for example, from 100° to 150° C. and preferably at temperatures of from 110° to 130° C.

In an alternative embodiment, silicic acid heteropolycondensate obtained after addition of the quantity of water stoichiometrically required for hydrolysis is isolated by evaporating off the solvent and stored until use. In this case, supports are coated by a process similar to that described above, the condensate optionally being dissolved beforehand in an organic solvent, such as acetone.

Coated substrates may be produced by standard methods, for example:

(a) dipping the support to be coated into a solution of the silicic acid heteropolycondensate or the precondensate and evaporating off the solvent;

(b) spraying a solution of the silicic acid heteropolycondensate onto the support to be coated and evaporating the solvent;

(c) introducing a solution of the silicic acid heteropolycondensate into containers or vessels and evaporating off the solvent.

Evaporation of the solvent may optionally be carried out under reduced pressure. The thickness of the silicone layer obtained does not have any effect on its serviceability.

Any materials may be used as supports, for example glasses such as boron silicate glass or quartz glass; minerals such as hydroxyapatite; ceramic materials such as porcelain, whiteware or chamotte; metals such as iron and aluminium; metal oxides such as iron oxide and aluminium oxide; wood; paper; carbon materials; plastics such as polyvinyl chloride, polyethylene or polypropylene, and organic high polymers such as cellulose or polysaccharides. The supports may have any geometric form. Standard commercially available Roux bottles are preferably used for the preparation of cell cultures.

In contrast to conventional coatings, it has been found to be unnecessary to pretreat the supports to be coated mechanically or to clean them chemically. A considerable saving of time and costs is obtained this way. Another advantage over known coatings lies in the fact that the silicic acid heteropolycondensates according to the invention adhere very firmly to the support so that the coated articles can easily be cleaned and repeatedly reused. Where cell cultures are prepared in Roux bottles, the bottles may be reused at least five times, whereas known products can only be used as non-reusable bottles. In addition, the articles coated in accordance with the invention are easy to sterilize, for example over prolonged periods at 100° to 120° C.

Preparations and coatings obtained from the silicic acid heteropolycondensates according to the invention are suitable for use as supports for the preparation of a variety of different single-cell or multiple-cell vegetable or animal tissue and cell cultures for scientific and technical purposes. For virological studies for example, it is possible to culture a variety of different types of cells, such as chickens' fibroblasts, monkeys' kidney cells, human amnion cells and permanent cell strains, for example Hela, KB and Detroit-6 strains.

For the culture of liver cells, the cells are pre-cultured for example in a suitable nutrient solution, such as Eagles-Modified-Medium, and then introduced in the form of a cell suspension into the vessel, for example a Roux bottle, coated with the silicic acid heteropolycondensate. To facilitate cell growth, the bottle is filled with a suitable nutrient medium and serum, for examples calf's serum, and/or embryonal extracts are optionally added. When the required stage of growth is reached, the cell fur is harvested by the addition of a dilute trypsin solution and the cell suspension removed from the vessel.

Tissue and cell cultures are prepared by standard methods as described, for example, by P. F. Kruse, Jr. and M. K. Patterson, Jr. in "Tissue Culture, Methods and Applications", Academic Press, New York, San Francisco, London (1973). The composition of the silicone coating is governed by the particular type of tissue or cell to be cultured. From his expert knowledge or after carrying out a few orienting tests, the expert will be able to select the silicic acid heteropolycondensates suitable for culture, i.e. having the necessary biocompatibility.

By virtue of the reactive coupling sites on their surface, the silicic acid heteropolycondensates according to the invention or the coatings produced from them may be used for various other applications, for example for chromatographic surfaces. A special application is the fixing of biochemical materials, for example antigens, antibodies, hormones, aminoacids, haptenes, proteins and enzymes. The biochemical materials are covalently coupled by known methods of organic chemistry and biochemistry; cf. for example U.S. Pat. No. 3,652,761. The stabilized biochemical preparations obtained are suitable for example as separating agents or adsorbents in biochemical processes, for example for radioimmunoassays, enzyme immunoassays or affinity chromatography.

In the fixing of biochemical materials and also in other fields of application, it can be of advantage to modify the functional group of the silicic acid heteropolycondensate by standard methods of organic chemistry. Depending on the reactivity of the functional groups in the compounds or materials to be coupled and in the layer of silicic acid heteropolycondensate, it is possible initially to derivatise the silicic acid heteropolycondensate and then to couple the required compound or the material. Suitable derivatising agents are, for example, amines, carboxylic acids, acid chlorides, thiocarbamates, thiocarbamic acid chloride, diazo compounds, esters and sulphides.

A polycondensate containing $\gamma$-aminopropyl groups may be modified for example by treating the polycondensate with an aqueous 2.5% by weight glutaraldehyde solution for 30 to 60 minutes at room temperature. The diazo derivative of the above-mentioned polycondensate may be produced for example by reaction with p-nitrobenzyl chloride, reduction of the nitro group to form the amine and di-azotisation with nitrous acid. If the silicic acid heteropolycondensate already contains anilino groups through the use of suitable functional silanes, it may be directly diazotised with nitrous acid. The reaction of amino groups of the silicic acid heteropolycondensate with thiophosgene gives the isothiocyano derivative.

The invention is illustrated by the following Examples.

SPECIFIC EXAMPLES

EXAMPLE 1

8.50 g of dimethyl diethoxy silane, 0.10 g of $\gamma$-aminopropyl diethoxy silane and 1.00 g of tetraethoxy silane were mixed in a solvent mixture of 25 ml of acetone and 25 ml of ethanol, followed by precondensation for 1 hour at room temperature. 1.00 g of water was then added, the solution was applied to a support to be coated and the solvent was evaporated off at 100° C. A firmly adhering, homogeneous coating was formed. On reaction with a pH color indicator, the coating showed a basic surface reaction on account of the amino groups present.

Example 2

8.50 g of dimethyl diethoxy silane, 0.66 g of bromopropyl triethoxy silane, 0.56 g of tetraethoxy silane and 5.00 g of a 10% solution of boron oxide ($B_2O_3$) in ethanol were dissolved in a solvent mixture of 11.8 g of acetone and 11.8 g of ethanol. The mixture was applied to a support to be coated and condensed by the addition of 3.00 g of water at 70° C. Removal of the solvent by evaporation left a homogeneous clear layer behind on the substrate.

Example 3

8.50 g of dimethyl diethoxy silane, 0.66 g of $\gamma$-aminopropyl triethoxy silane, 0.74 g of tetraethoxy silane and 2 g of a 5% solution of sodium methylate in methanol were mixed in a solvent mixture of 11.8 g of acetone and 11.8 g of ethanol, followed by precondensation for 12 hours in the absence of air. The reaction mixture was then applied to a support to be coated, 1 ml of water was added and condensation completed at 100° C. A firmly adhering coating was formed. On reaction with a pH colour indicator, the coating showed a basic surface reaction on account of the amino groups present.

Example 4

0.47 g of tetraethoxy silane and 10 g of a 10% solution of an acetone-soluble polycondensate of 0.25 g of diphenyl dichlorosilane and 0.18 g of $\gamma$-aminopropyl diethoxy silane were dissolved in 25 g of acetone and condensed to completion by the addition of 2 ml of water. Removal of the solvent by evaporation left an acetone-soluble white powder. For coating, a 1% solution of the polycondensate in acetone was applied to a support to be coated and the solvent was evaporated off at 50° C., leaving a clear, compact and firmly adhering coating which, on reaction with a pH-colour indicator, showed a basic surface reaction.

Example 5

0.32 g of tetramethoxy silane, 0.44 g of boric acid tributyl ester, 0.20 g of a 1% solution of sodium methylate in methanol, 24.40 g of a 10% solution in acetone of a soluble diphenyl dichlorosilane condensate and 0.05 g of $\gamma$-carbethoxy propyl triethoxy silane were dissolved in methanol. Following the addition of 0.50 g of water, the solution was applied to a support to be coated and condensed to completion by evaporating off the solvent at 35° C.

Comparison Example 4.25 g of dimethyl diethoxy silane, 0.47 g of $\gamma$-aminopropyl triethoxy silane and 4.67 g of tetramethoxy silane were mixed in 30 ml of methanol, followed by precondensation for 2 hours in the absence of air at room temperature. After the addition of 3.00 g of water, the solution was applied to a support to be coated and the solvent was evaporated off at 75° C. On account of the excessive $SiO_2$-content (approximately 60% by weight), a non-adhering porous layer was formed.

Application Example 1

7.5 ml of acetone, p.a., 7.5 ml of ethanol p.a. and 0.6 ml of tetraethoxy silane p.a. were mixed and stored in the absence of air (solution A). Similarly, 7.5 ml of acetone p.a., 7.5 ml of ethanol p.a. and 0.35 ml of $\gamma$-aminopropyl triethoxy silane were mixed and stored in the absence of air (solution B). A solution C was prepared by mixing 2.5 ml of acetone p.a., 2.5 ml of ethanol p.a. and 10 ml of dimethyl diethoxy silane and was also stored in the absence of air.

For precondensation, volume-equivalent quantities of solutions A, B and C were mixed and reacted for 2.5 hours at room temperature in the absence of air.

0.75 ml of water were added to 10 ml of the precondensate solution which was then poured into a Roux bottle. Condensation to completion was carried out over a period of 2 hours at 120° C. in a drying cabinet, the solvent evaporating off. The bottle thus internally coated was then rinsed with boiling water for 15 minutes and dried at 150° C.

Approximately 10⁷ cells of a liver cell preparation of the American Type Culture Collection (Rockville, Md., USA) were precultured for 24 hours at 37° C. in an incubator in 50 ml of Eagles-Modified-Medium. The water vapour and carbon dioxide partial pressure were selected in such a way that the composition of the nutrient solution remained unchanged. The cell suspension obtained was then poured into the Roux bottle coated as described above, followed by the addition of a suitable quantity of 10% calf's serum as nutrient medium. The culture process was then continued until the nutrient solution was exhausted. More nutrient solution could be added in order to obtain more cell growth. The dense cell fur ultimately obtained was harvested with dilute trypsin solution and removed from the Roux bottle.

Application Example 2

Solutions A, B and C were prepared in the same way as in Example 1. For precondensation, volume-equivalent quantities of these solutions were mixed, 0.2 ml of 0.1 N hydrochloric acid were added to 10 ml of the mixture obtained, followed by condensation for 7 minutes at room temperature. The Roux bottle was coated and liver cells were cultured in the same way as described in Example 1. Equally good results were obtained.

Application Example 3

The following starting solutions were prepared by mixing the individual components and stored in the absence of air:
Solution C: 2.5 ml of acetone, 2.5 ml of ethanol and 10 ml of dimethyl diethoxy silane
Solution D: 7.5 ml of acetone, 7.5 ml of ethanol and 1.2 ml of tetraethoxy silane
Solution E: 7.5 ml of acetone, 7.5 ml of ethanol and 0.7 ml of γ-aminopropyl triethoxy silane.

Equal volumes of solutions C, D and E were mixed and precondensed for 2 hours at room temperature.

The Roux bottle was coated and the liver cells cultured in the same way as in Application Example 1. Equally good results were obtained.

Application Example 4

A solution F was prepared from 3.5 ml of ethanol and 1.5 ml of diphenyl dichlorosilane. Equal volumes of solutions D, E and F were mixed and precondensed for 2 hours at room temperature in the absence of air.

The Roux bottle was coated and liver cells cultured in the same way as described in Application Example 1. Equally good results were obtained.

Application Example 5

As in Application Example 4, equal volumes of solutions D, E and F were mixed, 2 ml of water were added to 10 ml of the mixture obtained, followed by condensation for 2 hours. The high polymer precipitated was filtered off, the solvent was removed in high vacuum and the white powder left behind was stored in the absence of air.

0.1 g of the polycondensate were then dissolved in 50 ml of acetone. A Roux bottle is coated with 10 ml of the acetone solution obtained in the same way as described in Application Example 1. The culture of liver cells gives results as good as those obtained in Application Example 1.

We claim:
1. A process for the production of a silicic acid heteropolycondensate, comprising: simultaneously condensing
(a) at least one substituted silane corresponding to the general formula

$$SiR_n R''_{(4-n)} \quad (I)$$

in which R is selected from the group consisting of hydrogen, halogen, alkoxy and —NR'₂, wherein R' is hydrogen and/or lower alkyl, R" is selected from the group consisting of alkyl, alkenyl, aryl and aralkyl and n is an integer of from 1 to 3;
(b) at least one functional silane corresponding to the general formula $$SiR_n (R''' Y)_{(4-n)} \quad (II)$$

in which R is as defined above, R''' is selected from the group consisting of alkylene, phenylene, alkyl phenylene and alkylene phenylene; Y is selected from the group consisting of halogen, amino, anilino, aldehyde, keto, carboxy, hydroxy, mercapto, cyano, hydroxyphenyl, diazo, carboxylic acid alkyl ester, sulphonic acid (—SO₃H) and phosphoric acid (—PO₃H₂) groups and n an integer of from 1 to 3;
(c) at least one hydrolyzable silicic acid derivative corresponding to the general formula $$SiR_4 \quad (III)$$

in which R is as defined above, with the proviso that not all the radicals R are hydrogen; and
(d) optionally at least one compound selected from the group consisting of substantially involatile oxides of elements selected from the group consisting of Groups Ia to Va, IVb and Vb of the Periodic System and compounds of elements selected from the group consisting of Groups Ia to Va, IVb and Vb of the Periodic System which form a substantially involatile oxide in the presence of at least the quantity of water stoichiometrically required for hydrolysis and in the presence of a condensation catalyst and/or a solvent, the quantities in which said components (a) to (d) are used being selected in such a way that the silicic acid heteropolycondensate formed contains, based on oxide units from 60 to 90% by weight of said component (a), from 1 to 15% by weight of said component (b), from 1 to 30% by weight of said component (c) and from 0 to 40% by weight of said component (d), thereby producing a relatively nonporous coating containing a quantity of reacting coupling sites sufficient to fixedly attach a biological, chemical or biochemical material thereto.

2. The process of claim 1, wherein said starting components are reacted in a single stage until condensation is complete.

3. The process of claim 1, wherein said starting components are precondensed for 1 minute to 24 hours at −20° C. to 130° C., and are then condensed to completion in the presence of at least the quantity of water stoichiometrically required for hydrolysis of the remaining hydrolyzable groups in said reactants.

4. The process of claim 1 wherein said polycondensation reaction is carried out at a temperature of from −20° to +130° C.

5. The process of claim 1 wherein said polycondensation reaction is carried out at a temperature of from 0° to 65° C.

6. The process of claim 1 wherein said polycondensation reaction is carried out at ambient temperature.

7. The process of claim 1 wherein said silicic acid heteropolycondensate formed contains, based on oxide units, from 65 to 85% by weight of component (a), from 2 to 10% by weight of component (b), from 5 to 20% by weight of component (c) and from 0 to 20% by weight of component (d).

8. The process of claim 1 wherein an organic solvent is used.

9. The process of claim 8 wherein said organic solvent is selected from the group consisting of alcohols, ketones, ethers, amides and mixtures thereof.

10. The process of claim 1 wherein water, an acid, an inorganic base or an amine is used as the condensation catalyst.

11. The process of claim 1 wherein said condensation catalyst is added in quantity of up to 3% by weight, based on said reaction mixture.

12. The process of claim 1 wherein component (d) is selected from the group consisting of substantially involatile oxides and compounds which form substantially involatile oxides, of sodium, potassium, magnesium, calcium, boron, aluminium, lead, phosphorus, arsenic, titanium, zirconium and vanadium.

13. The process of claim 1 in which the compound forming a substantially involatile oxide is selected from the group consisting of inorganic acids, their esters, halides and salts, metal hydroxides, metal alkoxides and metal salts of volatile acids.

14. The process of claim 3, wherein said starting components are precondensed in the presence of a condensation catalyst.

15. The process of claim 3, wherein said starting components are precondensed in the presence of a solvent.

16. The process of claim 3, wherein said starting components are precondensed in the presence of a condensation catalyst and a solvent.

17. The process of claim 7, wherein said salicic acid heteropolycondensate contains from 75 to 80% by weight of component (a).

18. The process of claim 7, wherein said silicic acid heteropoly-condensate contains from 4 to 8% by weight of component (b).

19. The process of claim 7, wherein said silicic acid heteropoly-condensate contains from 9 to 12% by weight of component (c).

20. The process of claim 7, wherein said silicic acid heteropoly-condensate contains from 0 to 10% by weight of component (d).

21. The process of claim 1, wherein said applied coating is treated with water or steam at a temperature of 40° C. to 150° C. and/or heat treated at an elevated temperature from 100° C. to 150° C.

22. The process of claim 1, wherein said coating is heat treated at an elevated temperature.

23. The process of claim 1, wherein said coating is further heat treated at an elevated temperature.

* * * * *